（12） United States Patent
Chicchetti et al.

(10) Patent No.: US 9,198,270 B2
(45) Date of Patent: Nov. 24, 2015

(54) RADIOGRAPHIC IMAGING APPARATUS WITH DISTRIBUTED ANTENNA SYSTEM

(71) Applicant: Virtual Imaging, Inc., Deerfield Beach, FL (US)

(72) Inventors: Peter M. Chicchetti, Fort Lauderdale, FL (US); Carmine Pizzuto, Fort Lauderdale, FL (US); Christopher Duca, Cape Coral, FL (US); Freddie Lang, Fort Lauderdale, FL (US)

(73) Assignee: Virtual Imaging, Inc., Boca Raton, FL (US)

( * ) Notice: Subject to any disclaimer, the term of this patent is extended or adjusted under 35 U.S.C. 154(b) by 209 days.

(21) Appl. No.: 13/679,640

(22) Filed: Nov. 16, 2012

(65) Prior Publication Data

US 2013/0129048 A1    May 23, 2013

Related U.S. Application Data

(60) Provisional application No. 61/561,626, filed on Nov. 18, 2011.

(51) Int. Cl.
*H05G 1/08* (2006.01)
*A61B 6/00* (2006.01)

(52) U.S. Cl.
CPC ............... *H05G 1/08* (2013.01); *A61B 6/4405* (2013.01); *A61B 6/4452* (2013.01); *A61B 6/56* (2013.01); *A61B 6/547* (2013.01); *A61B 6/588* (2013.01)

(58) Field of Classification Search
USPC .......................................... 378/1, 21, 91, 95
See application file for complete search history.

(56) References Cited

U.S. PATENT DOCUMENTS

| 7,567,651 B2 | 7/2009 | Serceki et al. |
| 7,664,228 B2 | 2/2010 | Yi |
| 7,873,145 B2 | 1/2011 | Liu et al. |

(Continued)

FOREIGN PATENT DOCUMENTS

JP    2010197679 A    9/2010

OTHER PUBLICATIONS

Haynes, "A Primer on Digital Beamforming", Spectrum Signal Processing, www.spectrumsignal.com, Mar. 26, 1998, pp. 1-15.

(Continued)

*Primary Examiner* — Nicole Ippolito
*Assistant Examiner* — Hanway Chang
(74) *Attorney, Agent, or Firm* — Canon USA Inc. IP Division

(57) ABSTRACT

A radiation imaging apparatus includes a console that houses control circuitry and a computer; a radiation source attached to a movable arm, the movable arm being attached orthogonally to a column disposed adjacent to the console; and a wireless communication system that can communicate with a wireless radiation detector. The wireless communication system includes a plurality of antennas each of which is disposed within a predetermined distance from each other; the computer controls the communications system and the radiation detector so that the antennas transmit control signals from the console to the radiation detector or receive image signals from the radiation detector, and the antennas are positioned either within console immediately below a housing thereof or around the column so as to face a usable patient area, the usable patient area being an area surrounding the console where the radiation detector is positioned during an imaging operation.

18 Claims, 9 Drawing Sheets

(56) References Cited

U.S. PATENT DOCUMENTS

| 7,989,773 | B2 | 8/2011 | Jadrich et al. |
|---|---|---|---|
| 8,622,836 | B2 | 1/2014 | Nelson et al. |
| 2002/0150214 | A1 | 10/2002 | Spahn |
| 2009/0116431 | A1 | 5/2009 | Cadieux |
| 2013/0010928 | A1 | 1/2013 | Hannon et al. |

OTHER PUBLICATIONS

Cui, et al., "Energy Efficiency of MIMO and Cooperative MIMO Techniques in Sensor Networks", IEEE Journal on Selected Areas in Communications, Aug. 2004, pp. 1089-1098, vol. 22, No. 6.

Baker, et al., "Medical-Grade, Mission Critical Wireless Networks", IEEE Engineering in Medicine and Biology Magazine, Mar./Apr. 2008, pp. 1-10.

Freescale, "Medical Applications User Guide", 2010, <www.freescale.com/medical>, pp. 1-88.

Hanna, Salim, "Regulations and Standards for Wireless Medical Applications", Spectrum Engineering Branch, Industry Canada, Ottawa, Ontario, Canada, pp. 1-5.

Sheerer, N., "Engineering the Wireless Hospital: Mobility and Connectivity", Jul. 18, 2013, http://www.summitdata.com/blog/engineering-the-wireless-hospital-mobility-and-connectivity/.

"How to Check Wireless Signal Strength and Optimize WiFi Networks in Mac OS X", Dec. 28, 2011, http://osxdaily.com/2011/12/28/check-wireless-signal-strength-optimize-wifi-networks-mac-os-x/.

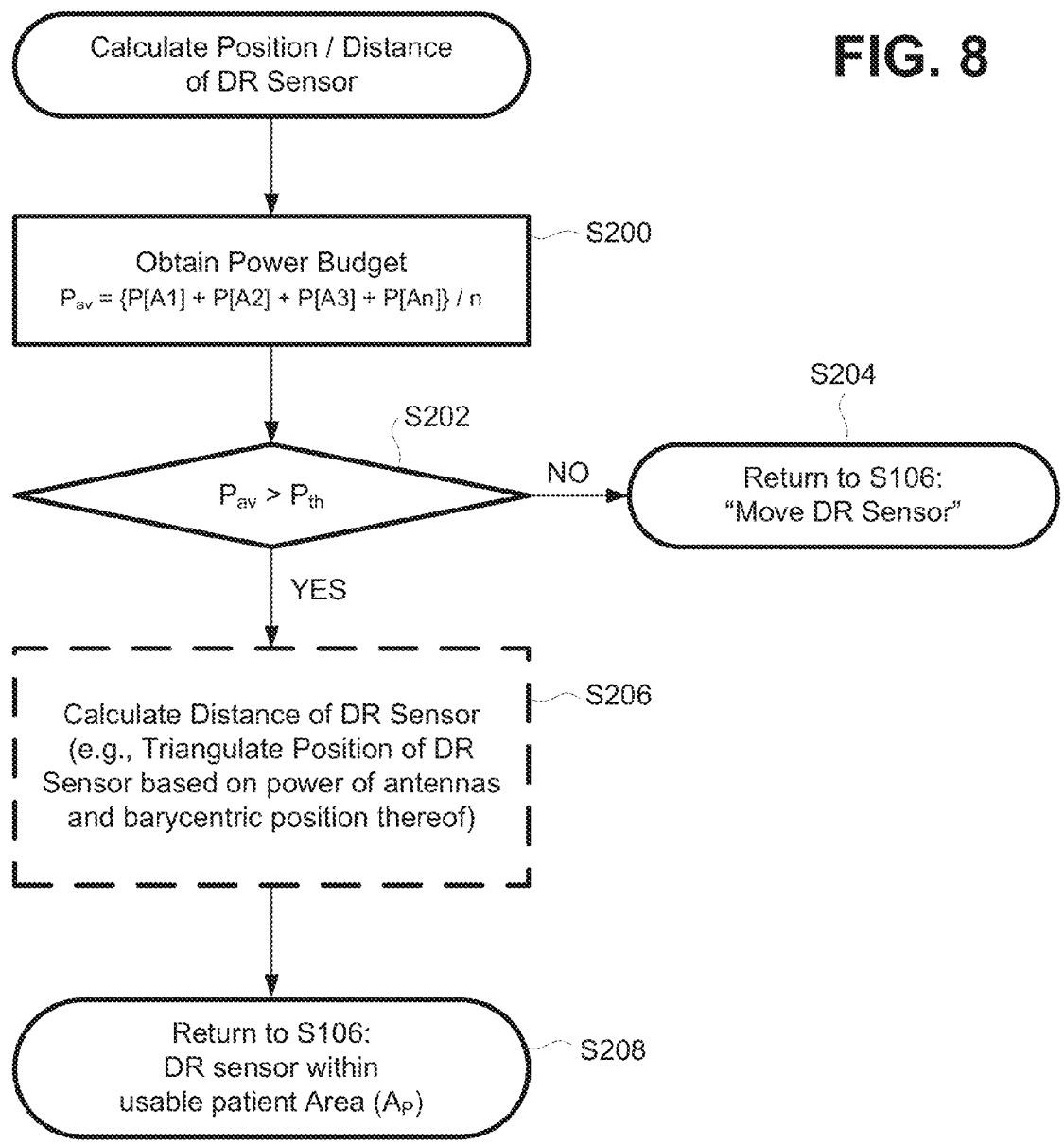

RADIOGRAPHIC IMAGING APPARATUS WITH DISTRIBUTED ANTENNA SYSTEM

CROSS REFERENCE TO RELATED APPLICATIONS

This application claims priority from Provisional Application No. 61/561,626 filed Nov. 18, 2011, the disclosure of which is hereby incorporated by reference herein in its entirety.

FIELD

The disclosure of this application relates generally to wireless communications for a radiographic imaging apparatus, and in particular to a radiographic imaging apparatus with a distributed antenna system (DAS) suitable for efficient communication between a wireless digital radiographic (DR) sensor and the radiographic imaging apparatus. The distributed antenna system may be applicable to stationary or mobile radiographic imaging apparatuses.

BACKGROUND

Conventional DR sensors, such as solid-state based flat panel detectors (FPDs), are well known for their advantages over traditional screen/film (S/F) cassettes. DR sensors are the current state of the art for medical and security imaging as these provide substantial advantages over traditional analog S/F based systems. Not only does digital radiography offer higher resolution and higher quality images, but it also permits substantially instant acquisition and analysis of captured images. Conventional DR sensors require cable connections at least for voltage supply, transmission of control signals, and transfer of image data. Cable connections, however, are not only an inconvenience for examining bed-bound patients, but also can hinder the use of DR sensors in sterile environments, such as trauma centers and operating rooms. To overcome the constraints presented by wired DR sensors, numerous implementations of wireless DR sensors have been proposed.

Patent Application Publication US 2002/0150214 A1 entitled "X-ray installation with wireless communication between the radiation receiver and control unit", by Martin Sphan (herein "Sphan"), discloses a transportable radiation receiver that communicates via a wireless communication link with a control device of the mobile imaging unit. Transmission and reception units for a bidirectional communication are provided at the radiation receiver and at the control device, respectively. According to Sphan, any optical or radio frequency (RF) communication technique may be suitable for fast transmission of relevant signals between the transmission and reception units, while allowing positioning freedom of the radiation receiver. Sphan does not consider any problems that are usually caused by free positioning of the radiation receiver.

U.S. Pat. No. 7,567,651 B2 entitled "directional antenna system for wireless x-ray devices" to Serceki et al., (herein "Serceki"), discloses a directional antenna system that employs a wireless link between an x-ray detector and an x-ray tube. Specifically, Serceki identifies that one problem with conventional x-ray systems is improper patient positioning which prevents the radiologist or technician from successfully imaging desired areas. Serceki also identifies that improper patient placement can create passive interference which will affect the wireless signals traveling between a transmitter and a receiver. To address these issues, Serceki discloses embodiments of an x-ray system in which directional antennas are positioned on both ends of the x-ray tube and at the x-ray detector. Specifically, the x-ray detector has one antenna that can communicate with the two antennas of the x-ray tube. The object of Serceki's invention is to assist with the proper placement and positioning of a patient for a targeted radiology session. It should be noted that in Serceki's patent, directional antennas at the x-ray tube and at the x-ray detector, located at positions where the patient would not block or interfere with the directionality of the antennas, are used to assist with the targeted placement and positioning of the patient. However, in mobile environments, for example, when examining bed-bound patients, it is very difficult to place the patient at a position where an antenna is not blocked or interfered by the patient.

U.S. Pat. No. 7,873,145 B2 entitled "Wireless Digital Image Detector" to Liu et al., (herein "Liu") discloses a digital detector that includes a plurality of antennas. The digital detector transmits image data via one or more antennas to a mobile x-ray unit that also includes one or more antennas. Liu recognizes that the distance between antennas of the detector and antennas of the mobile x-ray unit may vary due to movement of the detector. Liu also recognizes that phase and intensity of communication signals between antennas may also vary as a result of movement. However, Liu neither disclose what the distance constraints are, nor does it offer a specific solution to the problems caused by the change in distance and movement of the detector.

Thus, although wireless communication between a DR sensor and a remote device is known, one of the main problems that a wireless medical imaging system faces is interference, either passive created by a physical obstacle, or active created by another signal source. A wireless system in use at a medical facility must contend with a large number of physical obstacles and active sources of interference. For example, when a bed-bound patient cannot be moved, it is necessary to bring the medical radiography equipment to the patient and locate the DR sensor in positions where data transmission may be hindered. Likewise, in the case of certain traumas being treated in an emergency room (ER) or an operating room (OR), it is not always possible to position the patient appropriately in order to orientate the DR sensor in direct line-of-sight (LoS) with the mobile unit. In addition, in the context of the above-described problems afflicting the implementation of wireless mobile radiographic imaging, it should be noted that wireless medical imaging applications generate very large amounts of data (up to hundreds of megabytes per image in some cases). Thus, to ensure fast and accurate transfer of medical image data from a DR sensor to a remote location, reliable and high speed data links are required. However, wireless medical imaging applications must compete with numerous other wireless medical devices and networks. Some wireless medical devices transmit relatively small amounts of data, but are life-supporting and life-saving applications that deliver critical care to a patient. However, current wired and wireless networks lack the level of security, privacy and bandwidth required for handling the amounts of medical data being generated in current wireless medical environments. Accordingly, reliable wireless medical devices capable of low power consumption and low emission of RF radiation are required.

The present invention has been made in an effort to address the above-described problems.

SUMMARY

In accordance with at least one embodiment of the present invention, the instant disclosure is directed to, among other things, a radiation imaging apparatus comprising: a console that houses control circuitry and a computer; a radiation source attached to a movable arm, the movable arm being attached orthogonally to a column disposed adjacent to the console; and a wireless communication system that can communicate with a wireless radiation detector. The wireless communication system includes a plurality of antennas each of which is disposed within a predetermined distance from each other; the computer controls the communications system and the radiation detector so that the antennas transmit control signals from the console to the radiation detector or receive image signals from the radiation detector, and the antennas are positioned either within console immediately below a housing thereof or around the column so as to face a usable patient area, the usable patient area being an area surrounding the console where the radiation detector is positioned during an imaging operation.

Other modifications and/or advantages of present invention will become readily apparent to those skilled in the art from the following detailed description in reference to the drawings.

BRIEF DESCRIPTION OF THE DRAWINGS

FIG. 8 is a flowchart illustrating a process to determine whether the radiographic sensor is located within a usable patient area of the radiographic imaging apparatus;

DETAILED DESCRIPTION

In the following description, reference is made to the accompanying drawings which are illustrations of embodiments in which the disclosed invention(s) may be practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail as not to unnecessarily lengthen the present disclosure. Some embodiments or diagrams of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage device such as a magnetic or optical disk and disk drive for storing information and instructions, an optional user output device such as a display device (e.g., a monitor) for displaying information to the computer user, an optional user input device including alphanumeric and function keys (e.g., a keyboard) for communicating information and command selections to the processor, and an optional user input device such as a cursor control device (e.g., a mouse) for communicating user input information and command selections to the processor.

As will be appreciated by those of ordinary skill in the art, the present examples may be embodied as a system, a method or a computer program product. Accordingly, some examples may take the form of an entirely hardware embodiment, or an embodiment combining software and hardware aspects that may all generally be referred herein as a "circuit", "module" or "system". Further, some embodiments may take the form of a computer program product embodied in any non-transitory tangible computer-readable medium having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

Figure 1:
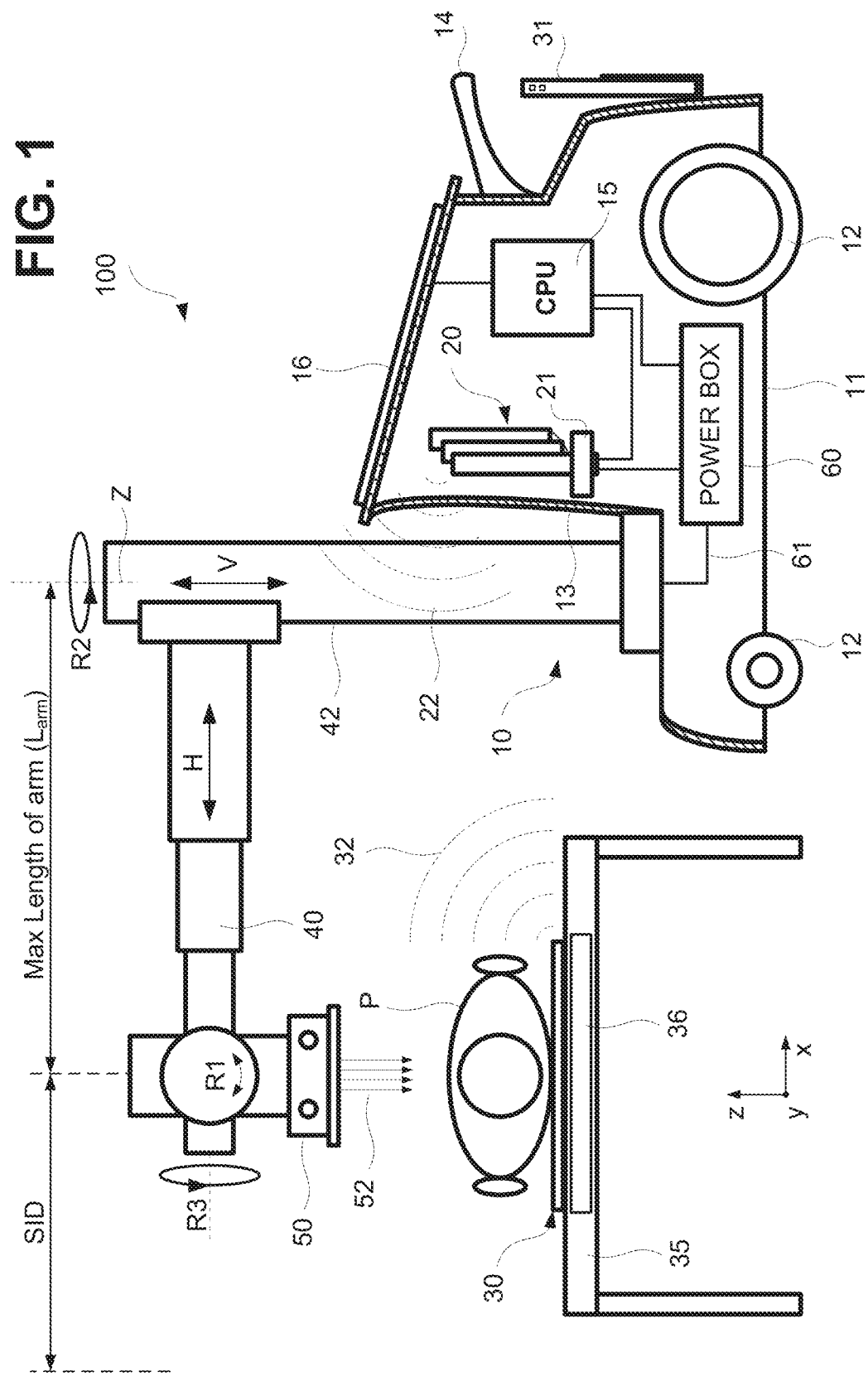
FIG. 1 illustrates an overview of a radiographic imaging system in accordance with a first embodiment of the present invention.

Referring now to the drawings, where like reference numerals refer to like parts, FIG. 1 illustrates an exemplary radiographic imaging system 100, in accordance with a first embodiment of the present invention.

As illustrated in FIG. 1, the radiographic imaging system 100 includes a radiographic mobile unit 10 (radiographic apparatus) and a wireless DR sensor 30. An example of the radiographic mobile unit is RadPRO® 40 kW Digital Mobile X-ray System distributed by Virtual Imaging Inc. or Fort Lauderdale, Fla.; and an example of the wireless DR sensor is the CXDI-70C Wireless Premium Flat Panel Detector available Canon Medical Systems a division of Canon USA Inc. of Lake Success, N.Y. The radiographic mobile unit 10 includes a console 11 and a radiation source 50. The radiation source 50 is attached to the console 11 via a support arm 40 (movable arm) and a column 42. At the bottom part of console 11 a chassis is mounted on caster wheels 12, so that the mobile unit 10 can be moved by maneuvering a handle 14. The chassis of the console 11 may be preferably made of an RF reflecting material (e.g., metals such a steel or aluminum). A housing 13 preferably made of RF transparent material is disposed on the chassis of console 11, so as to enclose therein electronic circuitry and components that serve to control the entire radiographic imaging system 100. On an upper surface of the console 11, a control panel 16 (user interface) implemented by a liquid crystal display (LCD), a keyboard, a pointing device, buttons, switches and the like is provided embedded (integrated) within the housing 13.

Enclosed within the housing 13 of the console 11 are included, for example, a central processing unit (CPU) 15 implemented by one or more microprocessors, a power box 60, and a distributed antenna system 20 connected to an antenna controller 21, each of which may be operatively connected to the control panel 16. The power box 60 may include, for example, a rechargeable battery and control circuitry to supply power for the entire operation of the mobile unit 10. The power box 60 may be connected to a non-illustrated external power supply via non-shown cabling, in a known manner. To supply power to devices connected thereto, the power box 60 may be connected by known cabling or circuitry to, for example, the CPU 15, the antenna controller 21, radiation source 50, control panel 16 and any other devices necessary for performing imaging operations therein. To supply power to the radiation source 50, the power box 60 is connected to cabling 61 that extends along the interior or exterior of column 42 and support arm 40. On the exterior of housing 13, console 11 may be provided with a compartment for carrying a secondary wireless or wired DR sensor 31.

In the first embodiment, the distributed antenna system includes a plurality of (3) antennas placed immediately inside (below) the housing 13 of console 11 at predetermined locations. In this embodiment the each of the antennas is a dual band vertically polarized omni antenna which operates either in a first band of 2.3-2.7 GHz or a second band of 4.9-6.1 GHz. A first antenna is placed in the front most part of the console 11 at a position substantially adjacent to the column 42, but in a manner that is not obstructed by the column 42. A second antenna is placed on the left most part of the console 11 approximately 5 inches or more away from the front most edge of the console 11; and a third antenna is placed on the right most part of the console 11 approximately 3 inches away or more from the front most part to the console 11. In this manner, the antennas are located at least 5 inches away from each other and distributed in a substantially triangular manner. A more detailed description of the antennas' positioning is provided below with reference to FIGS. 2 through 5.

In operation, the radiographic mobile unit 10 (wireless base station) is configured to wirelessly communicate with the wireless DR sensor 30 (wireless DR sensing unit), so as to obtain and process radiographic images of a patient P for display, storage or transmission. Specifically, during operation, the radiation source 50 generates radiation 52 by using high voltage power supplied from the power box 60 through cabling 61. An example of the radiation source 50 is an x-ray tube, and an example of the radiation emitted by the radiation source is x-ray radiation.

During operation, the direction and position of the radiation source 50 can be changed as desired. Specifically, the direction in which the radiation source 50 emits radiation can be changed by rotating the x-ray tube in a rotational manner as indicated by arrows R1 and R2. In addition, the radiation source 50 can be positioned at any position within a usable patient area which includes a semicircular area centered substantially on column 42. As used herein a usable patient area ($A_P$) may be defined as a semicircular area centered approximately on a barycentric position of the antenna array system 20 and with a radius equivalent to the maximum length of the support arm 40 ($L_{arm}$) plus the distance from the radiation source 50 to DR sensor 30 (SID: source to detector distance). The usable patient area $A_P$ will be described below in more detail. To place the radiation source 50 at any position and orientation within the usable patient area $A_P$, the support arm 40 can be telescopically moved in a horizontal direction H and in slideable a vertical direction V; and the column 42 can be rotated in rotational direction R2 around a longitudinal axis Z and may also be telescopically movable in the vertical direction V.

In operation, the DR sensor 30 is positioned directly facing the flow and direction of radiation 52 emitted from the radiation source 50; the patient P (or any other object) is positioned between the radiation source 50 and the DR sensor 30. As shown in FIG. 1, the radiographic mobile unit 10 can be used to obtain an image of the patient P, while the patient P is lying on a table 35. In this configuration, a radiation imaging operation is performed by placing the DR sensor 30 directly on the table 35 or in a compartment 36, such as Bucky tray. In this manner, the patient P or a part thereof may be placed directly in contact with the DR sensor 30, or somewhere in between the DR sensor 30 and the radiation source 50. As used herein, the patient P may represent either an object under inspection, or a human or animal subject under examination. In the case of a human or animal subject under examination, the patient P may also be standing in an upright position between the DR sensor 30 and the radiation source 50, at a predetermined distance from the DR sensor 30.

An image of the patient P or a predetermined part thereof is obtained when the console 11 controls the radiation source 50 and the DR sensor 30 to perform an imaging operation. Specifically, an operator may use the control panel 16 to run a program stored in a non-illustrated storage unit, so that when the program is executed by CPU 15 a control signal is sent from CPU 15 to radiation source 50 via wired connections (wire 61). Under the control from CPU 15, the radiation source 50 emits a predetermined amount of radiation 52 directed towards the patient P. As the same time, the CPU 15 controls the distributed antenna system 20 to send control signals 22 to DR sensor 30. The DR sensor 30, under wireless control from the console 11 receives control signals from CPU 15 to detect the intensity of radiation that passes through the patient P. That is, the radiation 52 emitted by the radiation source 50 passes through a region of interest (ROI) of the patient P; the DR sensor 30 detects the intensity of the radiation passed through the patient P and outputs a wireless image signal 32 which is received then by the distributed antenna system 20 of the radiographic mobile unit 10. In other words, the DR sensor 30 detects a spatial distribution of radiation intensity which has passed through the patient and coverts that radiation intensity into image data in accordance with the spatial distribution. The image data is then wirelessly transmitted to the radiographic mobile unit 10.

Some of the challenges in wirelessly controlling the DR sensor 30 from the mobile unit 10, and wirelessly transmitting the detected image signal from the DR sensor 30 to the radiographic mobile unit 10 include interference from other wireless devices, electromagnetic interference from surrounding wired devices and x-ray equipment, limited bandwidth of the wireless network connecting the DR sensor 30 and mobile unit 10, lack of line-of-sight between the DR sensor 30 and the receiving antenna of mobile unit 10 due to positioning of the sensor, and so on. More specifically, on one hand, in order to conserve power and prevent interference with other devices, the wireless DR sensor 30 must be able to transmit large amounts of image data using radio frequency signals at substantially low power levels. On the other hand, in order to minimize radiation exposure of a patient and to ensure secure transfer of image data crucial for diagnostic determinations, detected images must be transmitted without errors in a very short time. For example, in performing fluoroscopic imaging, a DR sensor must acquire high resolution (1024×1024) images at rapid acquisition rates of up to 30 fps (frames per second). These images are temporarily held in a local memory of the DR sensor, while being wirelessly transmitted from the DR sensor to the mobile unit 10. However, due to the interference and bandwidth limitations mentioned above, transmission of image data via wireless links tends to be prone to transmission errors and lost images. Thus, in the case of transmission errors, a patient is inevitably subject to additional radiation, so that a new image (or series of images) may be obtained. For these reasons, one of the central aspects of the present invention is to demonstrate that by using a distributed antenna system in which antennas are located at specifically predetermined positions within the radiographic unit, sensitivity of the receiving antenna system is increased, interference is minimized and communication between the DR sensor and the radiographic unit can be optimized within a predetermined usable patient area.

Figure 2:
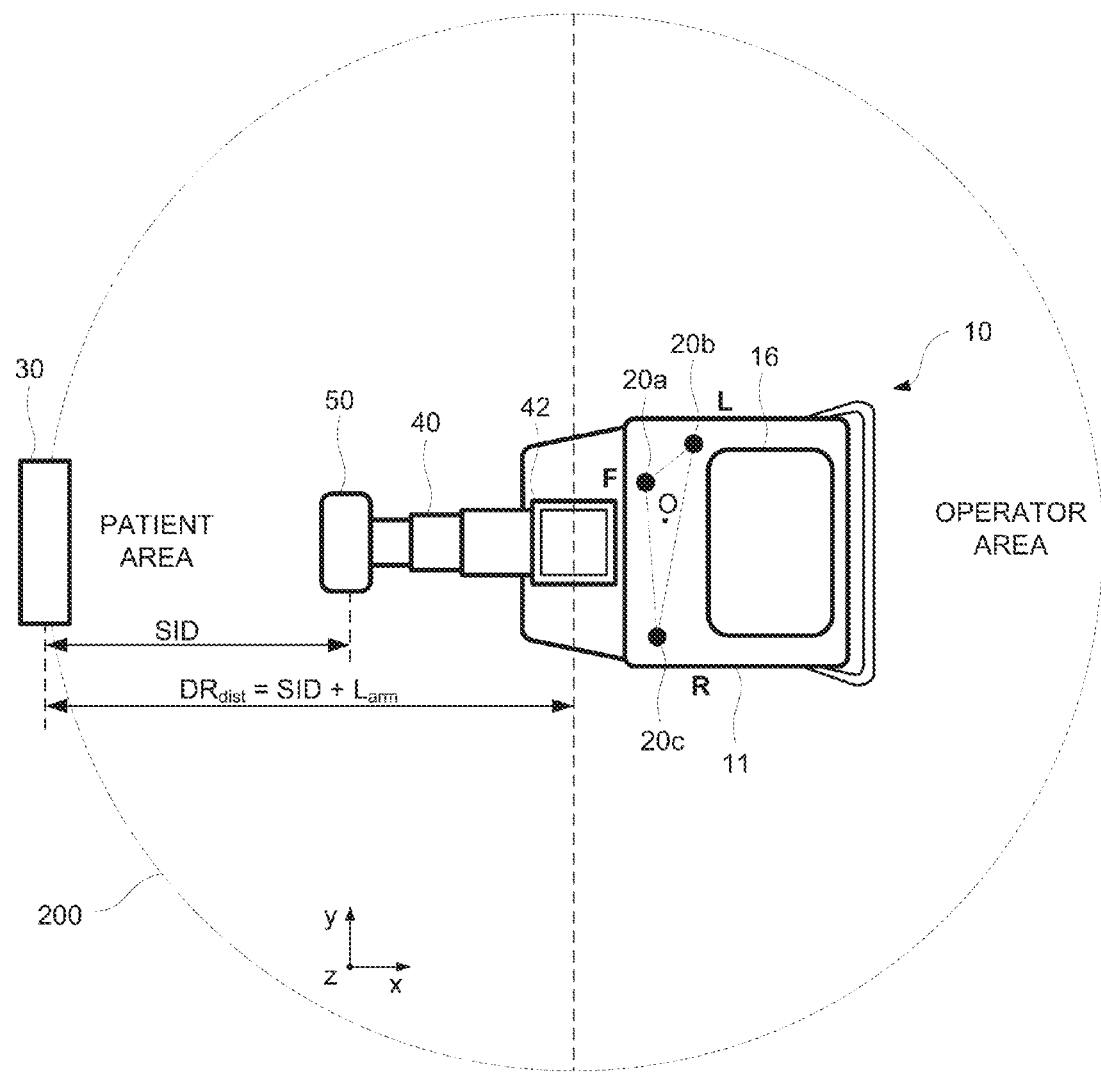
FIG. 2 illustrates a top view of a radiographic imaging apparatus and a spatial distribution of an area surrounding the apparatus, in accordance with the first embodiment of the present invention.
Figure 3:
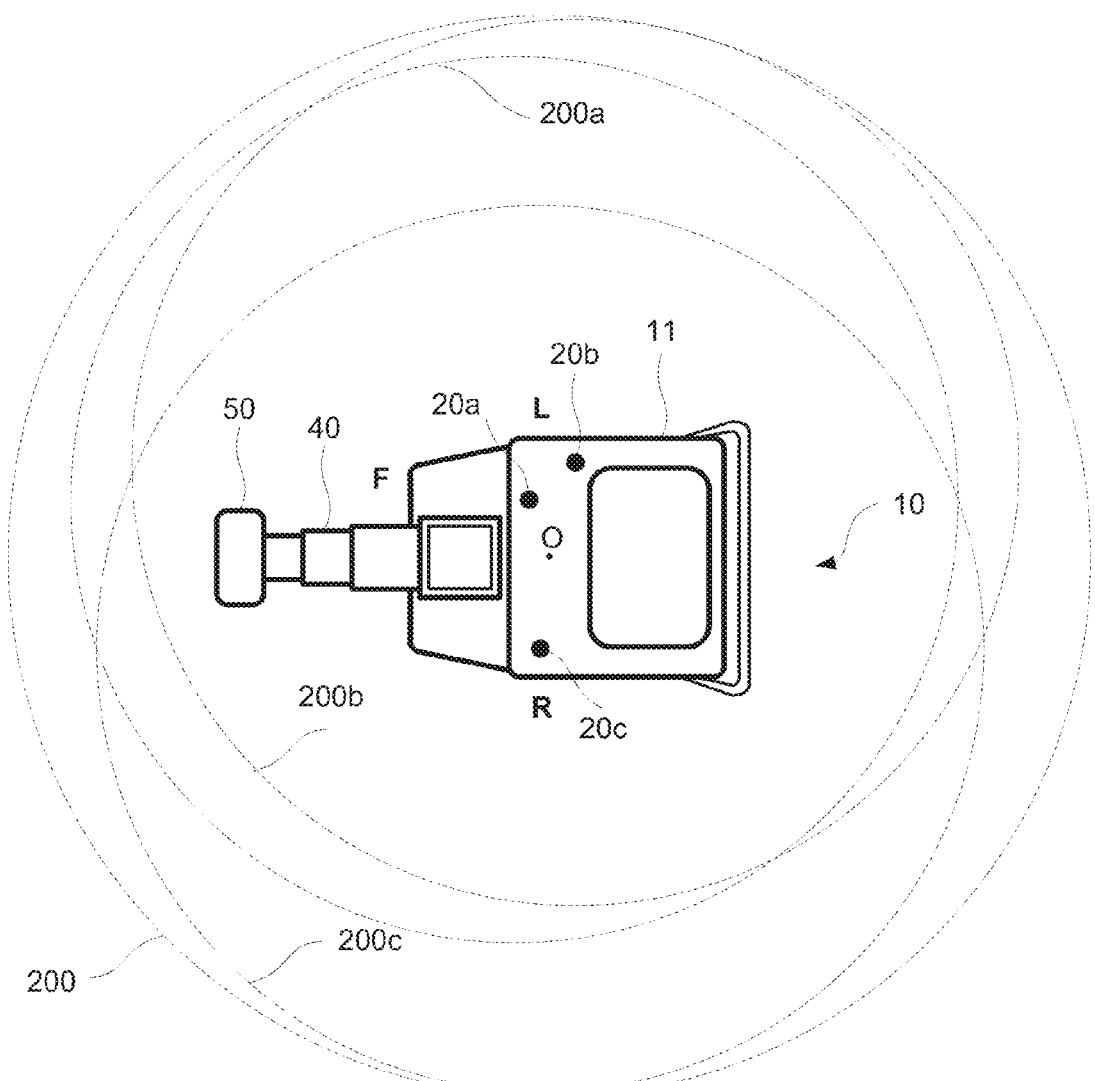
FIG. 3 illustrates a top view of the radiographic apparatus including a plurality of antennas configured to communicate with a radiographic sensor located at a predetermined distance from the apparatus, in accordance with the first embodiment of the present invention.

The concept of defining a usable patient area ($A_P$) will be now described by making reference to FIGS. 2 and 3. Specifically, assuming that the radiographic system 100 is configured to move from one location to another, for example, within the premises of a medical facility, such as a hospital, the radiographic system 100 may move from the emergency room to the trauma center, and then to an operating room, and so on. This means that the environment surrounding the imaging system 100 can change often; however, it is known that the only parameters that remain fixed are the physical dimensions of the mobile unit 10. Accordingly, one can use the fixed parameters of the mobile unit 10 to establish what may be considered a fixed-distance wireless network. More specifically, one can create a wireless network that is limited to a specific area where imaging operations are to be performed. FIG. 2 illustrates a top view of relevant parts of the radiographic mobile unit 10, and graphically represents the manner in which a usable patient area may be defined. In FIG. 2, the distributed antenna system (DAS) 20 of FIG. 1 is shown as having a plurality of antennas, including a first antenna 20a, a second antenna 20b and a third antenna 20c disposed at predetermined locations within the housing 13 of the console 11. Each of the antennas is dual band vertically polarized omni antenna which operates either in a first band of 2.3-2.7 GHz or a second band of 4.9-6.1 GHz. As shown in FIG. 2, the first antenna 20a is placed in the front (F) most part of the console 11 at a position that is not aligned with the column 42; the second antenna 20b is placed on the left (L) most part of the console 11 and approximately 5 inches away from the front most edge of the console 11; and the third antenna 20c is placed on the right (R) most part of the console 11 approximately 3 inches away from the front most part to the console 11. In this manner, the antennas are located at least 5 inches away from each other, and distributed within the chassis of the console 11 so as to form a polygon with thee corners.

In referring to FIG. 2, it is first considered that for practical reasons a DR sensor 30 should be placed at a distance no greater that the maximum length of the support arm 40 ($L_{arm}$) plus the source to detector distance (SID). Accordingly, by adding the SID to the maximum length of the support arm 40 ($L_{arm}$), a circumference 200 may be defined as the area in which the radiation source 50 of radiographic mobile unit 10 can operate in wireless communication with DR sensor 30. With this structure, as shown in FIG. 2, it can be said that the radius of the circumference 200 is approximately equivalent to the maximum distance at which the DR sensor 30 can be placed from the column 42 (the vertical axis Z of column 42 is assumed to be the center of circumference 200). To express it another way, the distance from which the DR sensor 30 communicates with the mobile unit 10 can be restricted to a distance no greater than the SID plus the maximum length of the support arm 40 ($L_{arm}$). Thus, a DR sensor distance may be defined as: $DR_{dist} \leq SID + L_{arm}$. Accordingly, in FIG. 2, a circumference 200 having a radius equivalent to the DR sensor distance $DR_{dist}$ is defined. The circumference 200 can be divided into a usable patient area (PATIENT AREA) including the front (F), left (L) and right (R) sides of the mobile unit 10, and a usable operator area (OPERATOR AREA) including the backside of the mobile unit 10.

Now using the DR sensor distance $DR_{dist}$, a wireless network can be established, as shown in FIG. 3. In FIG. 3, each antenna 20a, 20b and 20c can transmit and receive signals in a circular communication field within the circumference 200. More specifically, as shown in FIG. 3, using omnidirectional antennas, the first antenna 20a may generate a first circular radiation pattern 200a; the second antenna 20b may generate a second circular radiation patter 200b; and the third antenna 20c may generate a third circular radiation pattern 200c. In this manner, it is possible to establish reliable communications between the DR sensor 30 and the mobile unit 10 within the entire circumference 200. However, as it can be appreciated from FIG. 3, the usable operator area or area on the back of the console 11 (where the operator is positioned to control the mobile unit 10) can not be used for imaging operations. Thus, the antenna radiation patterns shown in FIG. 3 may not offer an entirely optimized solution to ensure completely reliable communications between the DR sensor 30 and the mobile unit 10. In particular, when omnidirectional antennas are used on the outer surface of the console 11 (e.g., externally attached to the housing 13), antenna radiation power and detecting sensitivity may be wasted on the back of the console 11. In addition, having the antennas on the external surface of console 11 may be aesthetically unpleasing; and more notably, the antennas may be damaged during movement of the mobile unit 10. Accordingly, in the first embodiment the plurality of antennas of distributed antenna system 20 are placed at predetermined positions immediately below (inside) housing 13. Advantageously, placing the distributed antenna system 20 within the housing 13 not only offers a safer and more aesthetically pleasing solution, but it also allows for beam forming and radiation pattern management as further discussed below.

Figure 4:
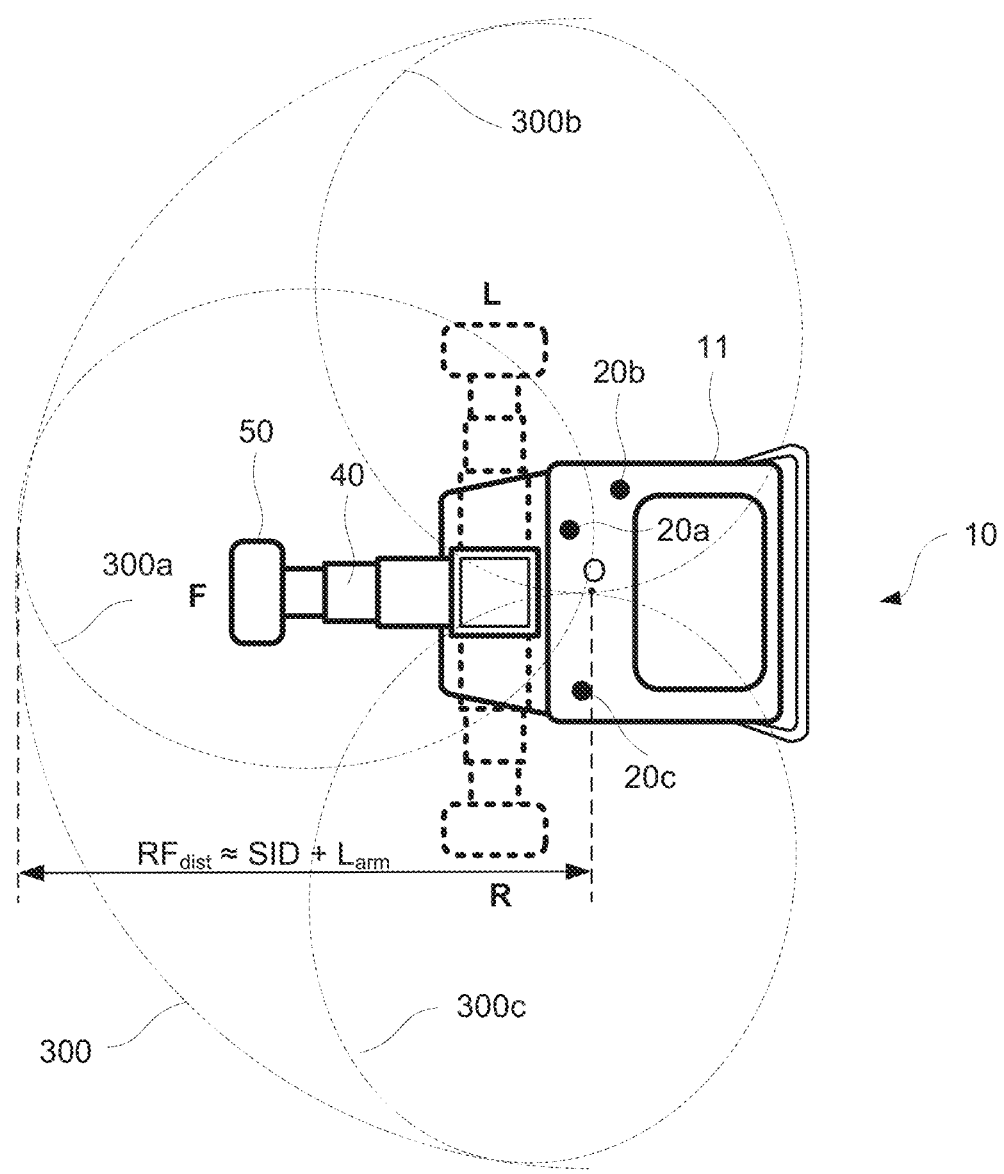
FIG. 4 illustrates a top view of the radiographic apparatus including a plurality of antennas configured to communicate with a radiographic sensor located within patient usable area, in accordance with the first embodiment of the present invention.

Specifically, as shown in FIG. 4, by placing the antennas at predetermined positions within (inside) the housing 13, the radiation patterns emitted from antennas 20a, 20b and 20c can now be strategically focused (directed) towards the patient usable area $A_P$. To simplify calculations, the front half of circumference 200 can be considered as the usable patient area. However, as illustrated in FIG. 4, when the support arm 40 is moved to the left side L and to the right side R the usable patient area may be even greater than a 180 degrees semicircular area. Now, considering that for optimal wireless communication (sending/receiving information) the antennas 20a to 20c should preferably be located facing the usable patient area on each side of the radiographic mobile unit 10, the inventors herein have determined that each of the plurality of antennas can be positioned at a specific predetermined location within the mobile unit 10 to optimize wireless communication between the DR sensor 30 and the mobile unit 10.

More specifically, according to the present embodiment, the plurality of antennas 20a, 20b and 20c are located at the front side (F), the left side (L) and the right side (R) of the console 11 of the mobile unit 10. A barycentric position (point) O is determined as the center of gravity (or average position) of all the antennas. A distance from the barycentric position O to the outer edge of the usable patient area of circumference 200 is assumed to be substantially equivalent to the above-discussed DR sensor distance ($DR_{dist}$). Accordingly, it can be now assumed that a required RF distance ($RF_{dist}$) to be covered by the distributed antenna system 20 is substantially equivalent to the DR sensor distance ($DR_{dist}$). Thus, the required RF distance ($RF_{dist}$) as used herein will be approximately equal to the distance from the center of gravity of the antennas (position O) to the furthest point where the DR sensor 30 can be located within the usable patient area $A_P$ to safely communicate with the distributed antenna system 20. Accordingly, the DR sensor distance ($DR_{dist}$) and the usable patient area are used to calculate a radiation pattern to be generated by each antenna 20a to 20c. Then, by combining the radiation pattern generated by each of the antennas with each other, a combined radiation sector 300 is formed; this combined radiation sector 300 will serve a communication field to be covered by the combined radiation patterns of antennas 20a to 20c. That is, the communication field established by each antenna is combined to form a combined radiation sector 300 that reliably covers communications between the DR sensor 30 and the mobile unit 10, and this communication field can be particularly concentrated and limited to the usable patient area. In other words, as long as the DR sensor 30 remains within the patient usable area, wireless communication between the DR sensor 30 and the mobile unit 10 can be effectively performed with minimized interference and reliable high speed. More specifically, as long as the DR sensor 30 remains within the patient usable area an effective line-of-sight (LoS) between the distributed antenna system 20 and the DR sensor 30 can be guaranteed. As used herein, "an effective LoS" may include not only an optical or direct line-of-sight path, but also a multipath line-of-sight as further discussed below.

In FIG. 4, the first antenna 20a located in the front most part of the console 11 is configured to create a first RF communication field (radiation pattern and receiving sensitivity field) 300a; the second antenna 20b located at the left side of the console 11 is configured to generate a second RF communication field 300b; and the third antenna 20c located at the left side of the console 11 is configured to generate a third RF communication field 300c. Each of the first to third RF communication fields 300a to 300c are concentrated in regions of the usable patient area, and these regions overlap each other to cover the entire patient usable area 300. In addition, each communication field 300a to 300c is optimized to radiate in a RF distance at least equal to the SID plus the length of the support arm 40 of the mobile unit 10. However, as illustrated in FIG. 4, it should be noted that each communication field 300a to 300c is not necessarily centered on its respective antenna. Instead, the communication fields 300a, 300b and 300c are distributed at the front F, left L and right R sides of the mobile unit 10 in a radial manner such that each of the communication fields meets (overlaps) the others at the barycentric position O of the plurality of antennas. To achieve this specific distribution of antenna radiation patterns, omnidirectional antennas may be placed immediately below (inside) the housing 13 of console 11 at different positions therein. In order to optimize RF transmission, it is desirable that housing 13 be made of an RF transparent material. In this manner, an equally distributed RF communication field equivalent to a at least 180 degrees antenna sector is created to cover the entire usable patient area $A_P$ so that communication between the DR sensor 30 and the mobile unit 10 can be reliably performed from any location within the usable patient area $A_P$. In this manner, the radiographic mobile unit 10 can not only reliably communicate with the DR sensor 30, but it can also determine if the DR sensor 30 is within the usable patient area $A_P$ before initiating an imaging operation.

The general technical premise for achieving the advantageous effects of effective wireless communication within the at least 180 degrees antenna sector, as described above, can be understood from the following discussion. It is known from general RF theory that the total average power consumption along a signal path depends on the distance that the signal travels and the amount of space where the signal spreads. In the simplest form, if a sinusoidal waveform is emitted by an isotropic point source, it would propagate radially in free space in all directions (360 degrees). If the emitted power is $P_R$ Watts (W), at a distance R meters away from the isotropic point source, the density of the power per unit area is given by $P_d=[P_R/4 \pi R^2]$ in $W/m^2$.

Similarly, it is known that an omnidirectional antenna radiates and receives signals equally in all directions in one plane. Accordingly, the power radiated by an omnidirectional antenna within an equivalent area $A_R$ is $P_{360}=A_R[P_R/4 \pi R^2]$. In the present case, as described above in reference to FIGS. 2 and 3, it is desirable that a communication field equivalent to an at least 180 degrees sector be concentrated on the front of the mobile unit 10. That is, it is desirable that the communication field be concentrated onto the patient usable area 300, which is equivalent to an at least 180 degrees antenna sector. Accordingly, still referring to FIGS. 2 and 3, it is considered highly advantageous if the power emitted by an antenna located at the barycentric position O could be focused within the patient usable area. To do that, it is assumed that the total power of an omnidirectional antenna can be directed (or concentrated) into a 180 degrees sector, by directing the radiation field of each antenna 20a, 20b and 20c towards the usable patient usable area, rather than emitting in a 360 degree radius. Accordingly, the power density concentrated onto an at least 180 degrees antenna sector is now given as $P_{180}=A_R [P_R/2 \pi R^2]$. Specifically, since the power originally spread in a 360 degree area of radius R is now concentrated in half that area, the power of the 360 degree area is now doubled (folded). That is, $P_{180}=P_{360} \times 2 = 2 A_R[P_R/4 \pi R^2]=A_R [P_R/2 \pi R^2]$. As a result, it can be seen that concentrating the power density from a 360 area of a radius R into a 180 degrees sector of radius R increases the total power in the 180 degrees sector by 3 decibels (dB), which, when attenuation losses and other considerations are accounted for, is equivalent to an approximately 40% increase in the sensitivity of the antenna system 20 that covers the 180 degrees sector of radius R, as compared to the same antenna system covering a circular area of radius R.

In order to concentrate the radiation pattern from an ominidirectional antenna towards a directional lobe radiation pattern, in the present embodiment, each of the antennas 20a, 20b and 20c are located immediately below (inside) the housing 13 of the console 11, so that a reflection plane is created by the components located within the console 11. Specifically, each antenna is positioned at a predetermined position at the front side F, the left side L and the right side R of the console 11 immediately below the housing 13. In addition, holding brackets made of RF transparent material are used to attach each antenna to the chassis of console 11; and high quality lossless RF cables are used to connect each antenna to the electronic circuitry (controller 21) within the console 11. As necessary, support plates or holding elements may be added within console 11 for appropriate placement of the antennas. Support plates may be designed of RF reflecting material, and these plates can be arranged to direct the reflected RF towards the patient usable area. One of ordinary skill in the art would know how to appropriately connect and attach the plurality of antennas within the housing of console 11. Notably, it is preferable that each antenna may be placed at a position where minimum RF interference exists in the direction facing the usable patient area, and RF reflection exists in the direction opposite to the usable patient area. When the antennas are disposed in this manner, part of the RF field radiated by the antennas reflects off of the components located inside the console 11 (e.g. it reflects off of the computer, power box and other circuitry), and is directed towards the front, left and right sides of the console 11. In addition, when the chassis is made of RF reflecting material, the chassis may also provide an additional reflecting surface for the radiation energy emitted form the antennas. Thus, the chassis and components residing within the housing 13 of the console 11 effectively act as a reflecting plane for part of the energy radiated by the antennas 20a, 20b and 20c; and the reflected energy effectively adds to the energy already radiated towards the front, left and right sides of the console 11. In addition, to improve the reflecting effect, reflective panels (e.g., semicircular RF reflecting panels) made of RF reflective material may be used in the vicinity of each antenna 20a, 20b and 20c respectively at a position opposite to the usable patient area. In this manner, by using a reflection plane in the vicinity of each antenna, each antenna can act as a highly directional antenna, which can concentrate its radiation pattern and its RF receiving sensitivity onto the usable patient area $A_P$. When comparing to the distributed antenna system illustrated in FIG. 3, test results (see FIGS. 9A-9D) indicate that in addition to enhancing antenna sensitivity and concentrating the radiation pattern of the antennas onto the usable patient area, the effective RF radiation distance of the distributed antenna system may be increased. In this manner, antennas that use relatively low power can be used to avoid excessive use of limited power resources in the mobile unit 10.

The power of each antenna necessary to effectively communicate with the DR sensor 30 located within the usable patient area $A_P$ can be calculated based on the above described parameters (SID and $L_{arm}$) of the mobile unit 10. Now solving for the distance R from the power density formula of the 360 degrees area with a radius R, one can obtain the distance R in terms of the power density for 180 degrees sector. Specifically $R_{360}=\sqrt{[(4\pi P_R)/(P A_R)]} \rightarrow R_{180}=\sqrt{([(2\pi P_R)/(P A_R)]}$. Or, put in another way, the distance R necessary to concentrate the radiated power of an RF antenna onto a 180 degree sector $R_{180}$ can be generalized by $R_{180}=\sqrt{2}\times R_{360}$. The distance $R_{360}$ can be derived from the above described DR sensor distance in terms of the physical parameters of the mobile unit 10. In most cases, chest radiography, for example, is commonly performed with a 72-inch (182.88 cm) SID, and the dimensions of the support arm 40 ($L_{arm}$) can be known from the manufacturer's specifications. SID parameters for each type of radiographic operation are generally available from sources of standardized and regulatory information, such as the U.S. Food and Drug Administration (FDA). That is, the source to radiation detector distance is a radiation distance generally established by regulatory agencies such as the FDA. Accordingly, the $DR_{dist}$ can be adjusted depending on the type of radiography imaging being performed.

Figure 5:
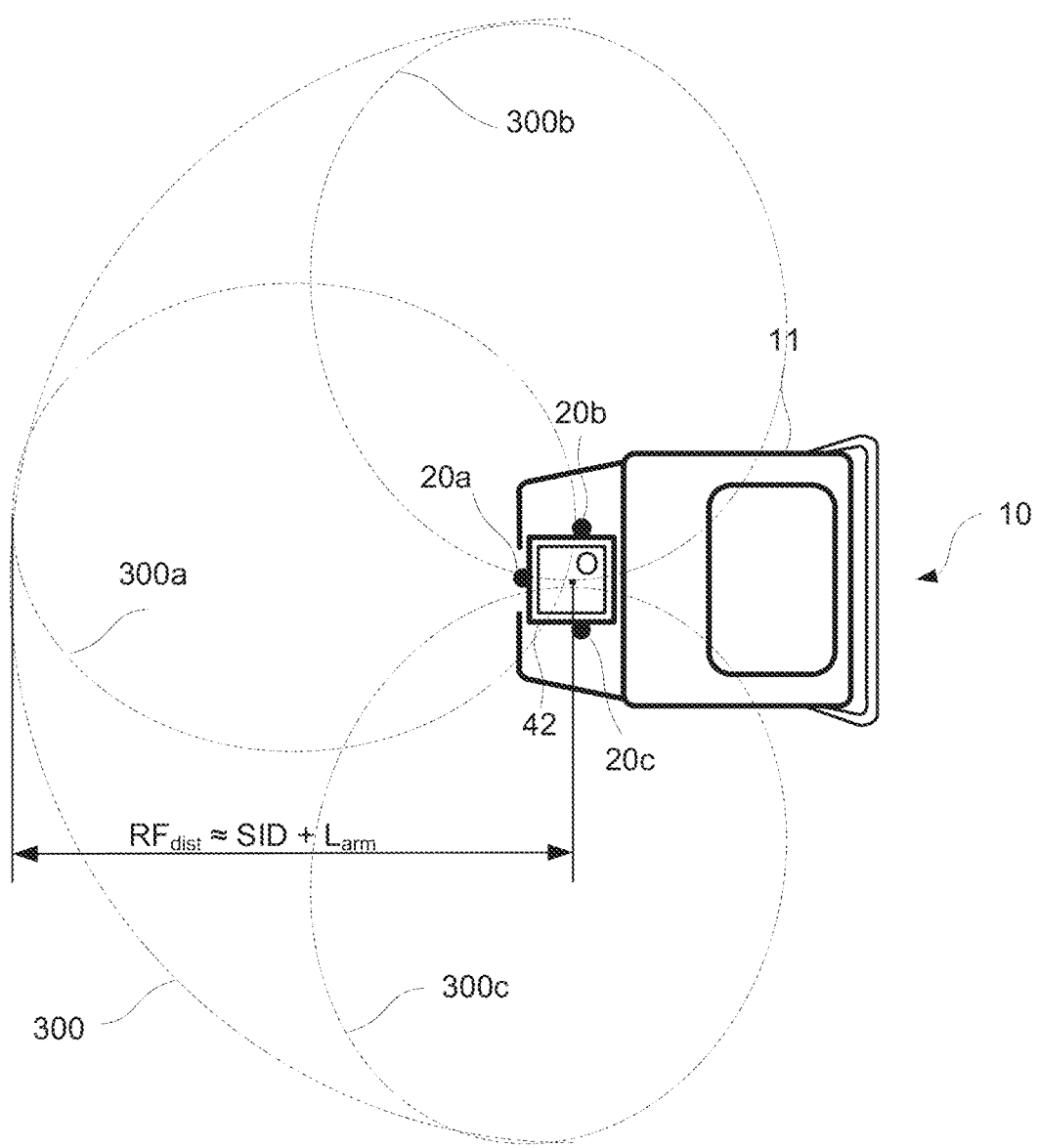
FIG. 5 illustrates a top view of the radiographic apparatus including a plurality of antennas configured to communicate with a radiographic sensor located within patient usable area, in accordance with a second embodiment of the present invention.

FIG. 5 graphically illustrates the concept of establishing a combined antenna sector by combining individual communication fields (radiation patterns) of a plurality of antennas, according to a second embodiment. The structure of the antenna distribution between FIG. 4 (first embodiment) and FIG. 5 (second embodiment) is substantially similar to each other, and thus unnecessary description will not be repeated. In FIG. 5, only relevant parts of the mobile unit 10 are shown for ease of illustration. One notable difference between the embodiment of FIG. 4 and that of FIG. 5 is that the plurality of antennas 20a, 20b and 20c are now located in the front side, left side and right side of column 42, respectively, instead of inside the housing 13. In this manner, the surfaces of the column 42 will now act as reflecting planes. That is, for each antenna 20a, 20b and 20c, the front, left and right surface of column 42 can be used as RF reflecting planes. In order to allow for sufficient freedom of movement in the vertical direction V (see FIG. 1), the antennas may be preferably placed at a height that does not prevent movement of the support arm 40 in the vertical V or rotational R2 directions. Similar to the embodiment of FIGS. 1 and 4, in the embodiment of FIG. 5, the required RF distance and the usable patient area 300 is used to calculate (or estimate) a radiation pattern for each of the antennas 20a, 20b and 20c. In the embodiment of FIG. 5, the longitudinal axis Z of the column 42 may be considered as barycentric position O. Although it is recognized that, in the second embodiment, the barycentric position O of the antennas 20a-20c has shifted by a relatively small distance, wireless communication between the DR sensor 30 and the mobile unit 10 can still be reliably maintained because the antennas are configured to cover an equally distributed RF communication field equivalent to a 180 degrees or greater antenna sector.

The concept of a "distributed" antenna system, as used herein, refers first to the fact that a plurality of antennas are spatially distributed and located at predetermined positions within the radiographic mobile unit. Second, the concept of "distributed" antenna system refers to a communication technique in which all antennas transmit and receive signals simultaneously. Third, the concept of "distributed" antenna system refers to the fact that radiation patterns of antennas are selectively distributed over the usable patient area. Implementation of the distributed antenna system can be modeled after the multiple input multiple output (MIMO) scheme. However, because in most cases there will be multiple antennas only on the mobile unit 10 and a single antenna at the side of the DR sensor, the distributed antenna system in the first and second embodiments are more like single input multiple output (SIMO) in one direction, and multiple input single output in the other direction (MISO).

MIMO uses multiple antennas to send multiple parallel signals from a transmitter to a receiver. Similarly, the multiple antennas are used to receive signals from a single antenna or multiple antennas. In typical environments, emitted wireless signals bounce off of interfering surfaces and advance to their destination in different directions and arrive to the destination at slightly different times. This is known as a multipath transmission. For antennas that require direct line-of-sight, multipath communication is not desirable because the different signals may interfere with each other, create noise and are weakened by the time they reach their destination. With MIMO, however, special algorithms or signal processing techniques are used to sort out and add the multiple signals received at the different antennas so that the original signal can be reproduced by averaging signals. Specifically, with MIMO, each multipath signal is treated as a separate channel over which signals are transmitted or received. Thus, even if only a few signals are received a reliable signal can be obtained by adding the received signals and obtaining an average. A more detailed description of transmission schemes used in MIMO can be found in readily available literature in technical publications. For example, Cui et al., in an article entitled "Energy-Efficiency of MIMO and Cooperative MIMO techniques in Sensor Networks", published by the IEEE Journal on Selected Areas in Communications, Vo. 22, No. 6, August 2004, which is incorporated herein by reference, offers a detailed description of modulation and transmission strategies to minimize the total energy consumption required to send a given number of bits over a certain distance.

However, MIMO is only example of a manner in which a distributed antenna system may be implemented. Digital spread spectrum (DSS) ant orthogonal frequency division multiplexing (OFDM), which also take advantage of multipath communications, may also be used to implement the distributed antenna system of the first or second embodiments. Accordingly, the embodiments disclosed herein are not limited to any specific manner in which the distributed antenna system may be implemented. Since the concept of using MIMO as a preferable example of forming a distributed antenna system is known, no further description is provided in reference to this topic.

Figure 6:
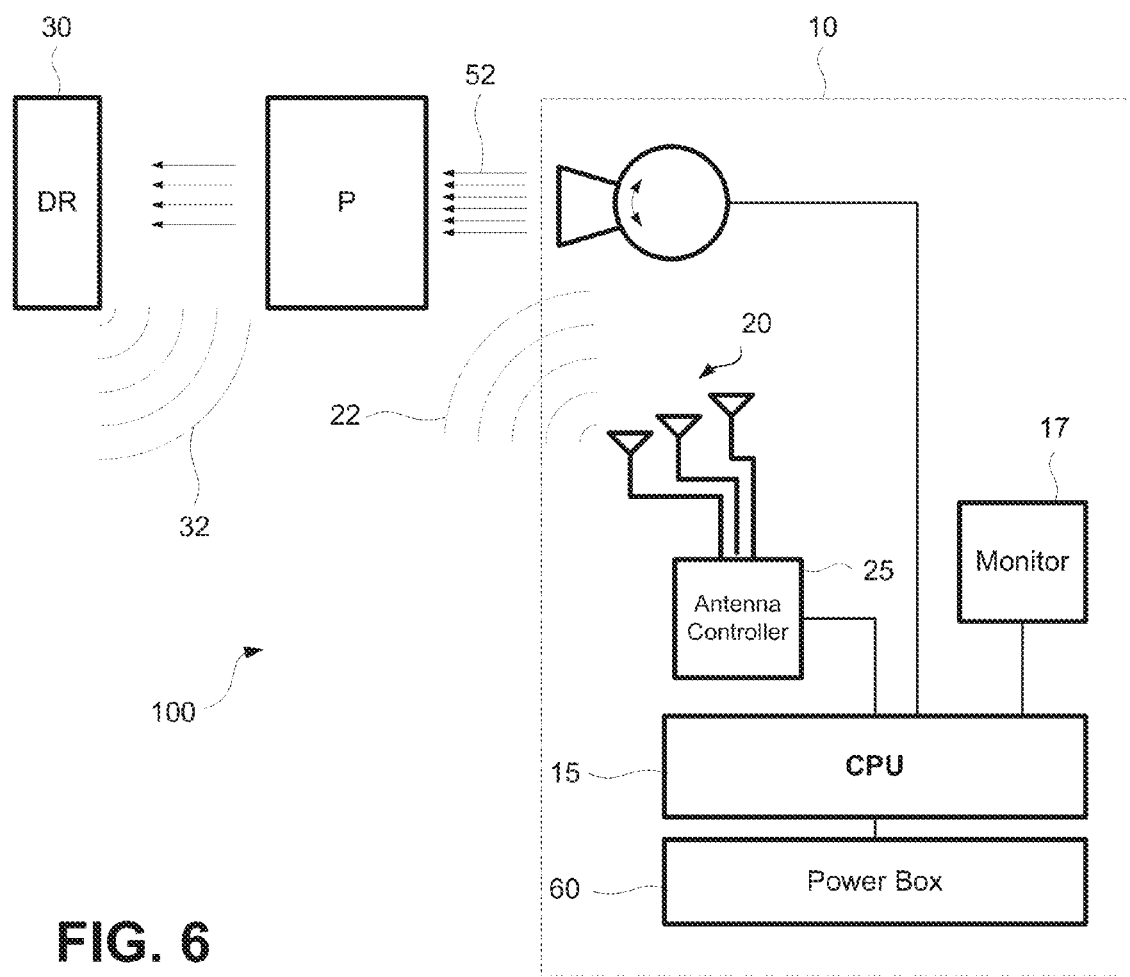
FIG. 6 is a block diagram of the radiographic imaging system in accordance with embodiments of the present invention.
Figure 7:
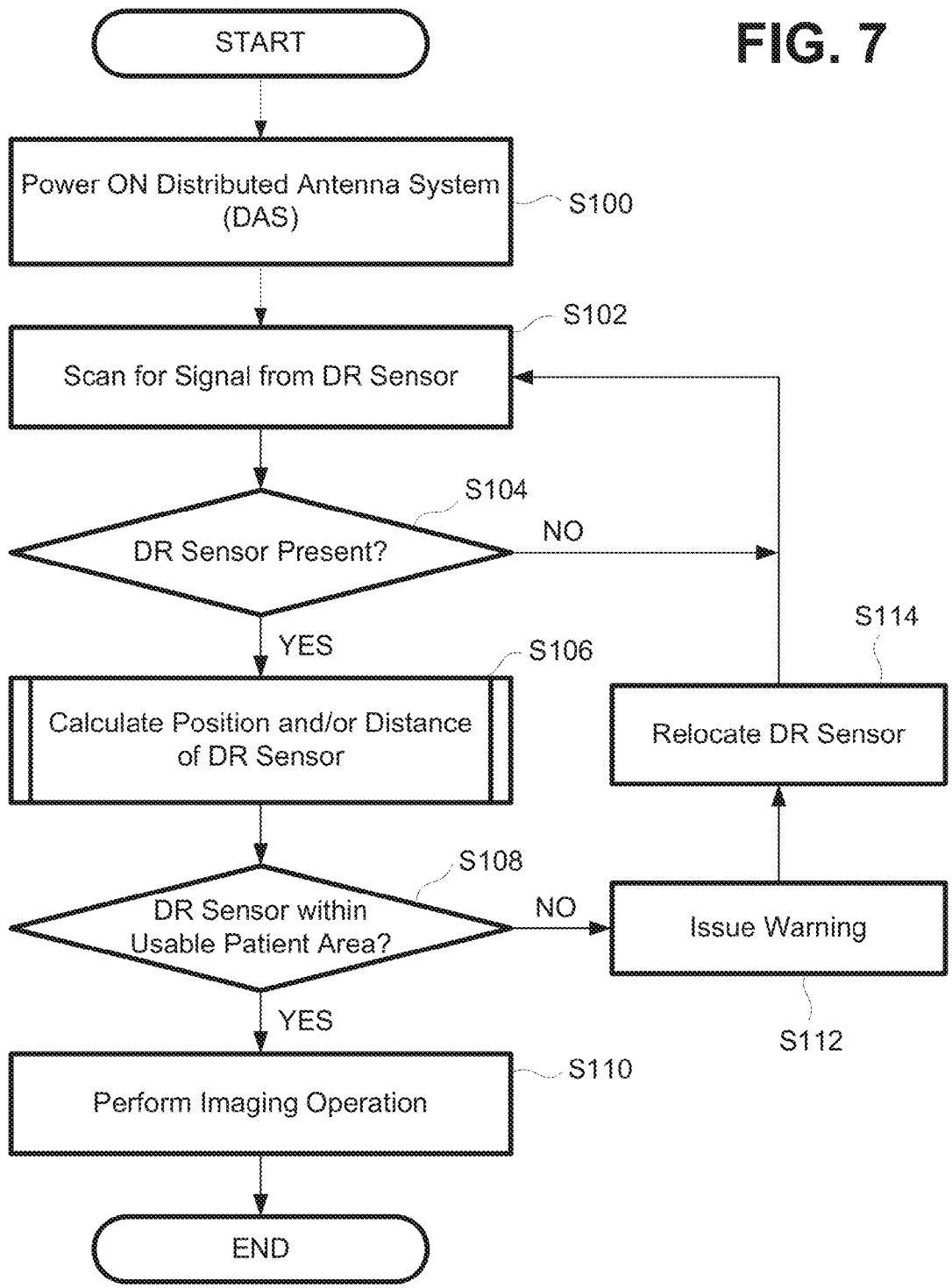
FIG. 7 is a flowchart of an exemplary process performed by a radiation imaging apparatus to establish communication with the radiographic sensor to acquire data from the radiographic sensor via a distributed antenna system, in accordance with embodiments of the present invention.

Turning now to FIGS. 6 through 8, a description will be provided of a method in which an imaging operation may be performed by a radiographic mobile unit equipped with the distributed antenna system in accordance with the embodiments of the present invention. Specifically, FIG. 6 illustrates a representative block diagram of the radiographic imaging system shown in FIG. 1. As illustrated in FIG. 6, the radiographic imaging system 100 preferably includes a mobile unit 10 equipped with a distributed antenna 20, which can communicate with a wireless DR sensor 30 to acquire image data and to process the image data in CPU 15 for display in a monitor 17, which is part of the control panel 16. In FIG. 6, similar to FIG. 1, the mobile unit 10 is power by a power box 60 to supply power to devices connected thereto. A radiation source 50 attached to the mobile unit 10 via a support arm 40 and column 42 (shown in FIG. 1) emits x-ray radiation 52 directed onto a region in which an object or subject P is positioned. A portion of the radiation 52 passes through the subject P and impinges on a surface of the DR sensor 30, in a known manner. As will be appreciated by those of ordinary skill in the art, the DR sensor 30 will convert the radiation received on its surface to electric signals and form an image signal in a known manner. The image signal will then be electronically output and wirelessly transmitted to mobile unit 10, in accordance with the wireless communication scheme of the above described embodiments.

However, prior to being able to perform an imaging operation, the mobile unit 10 is configured to ensure that the DR sensor 30 can effectively communicate with the distributed antenna 20. To that end, FIGS. 7 and 8 illustrate an exemplary flow process performed by the mobile unit 10 prior to initiating an imaging operation. Prior to initiating the flow process of FIG. 7, it is assumed that a DR sensor 30 has already been registered (paired) with the mobile unit 10, and that an operator intends to perform an imaging operation with the mobile unit 10. At step S100, the distributed antenna system 100 is power on, and the flow proceeds to step S102. At step S102, the distributed antenna system 30 under the control of CPU 15, scans for a signal from the DR sensor 30. Here any of a known scanning technique can be used. For example, a determination can be made by a hardware or software as to whether a RF signal above a predetermined dBm threshold is received in at least one of the antennas. Accordingly, after the scan made in step S102, the process flows to step S104 and determines whether a DR sensor is present in the vicinity of the mobile unit 10. If a DR sensor is not present (NO at S104), the flow process returns to step S102 and repeats the scanning until a DR sensor is detected. When a DR sensor is present somewhere in the vicinity of the mobile unit 10 (YES at S104), the process advances to step S106. At step S106, based on predetermined parameters, the CPU 15 calculates (makes an estimation) of the distance and/or position of the DR sensor.

The calculation of step S106 is explained with reference to FIG. 8. In FIG. 8, once a DR sensor has been detected in the vicinity of the mobile unit 10, at step S200, the CPU 15 can obtain a power budget. Specifically, the CPU 15, during the scanning process, can record the power level (dBm) detected by each antenna 20a, 20b, 20c. Once the power level detected by each antenna is recorded, an average ($P_{av}$) of the power received at the antenna system 20 can be calculated by adding the power from each antenna and dividing it by the number of antennas. In this calculation, any provisions, such as filtering or equalizing, for reducing the noise factor from known or assumed interference sources can be included. Once a power average is obtained, the flow process advances to step S202 where a determination is made whether the power average meets a power threshold ($P_{th}$). The power threshold may be established beforehand based on the known parameters of the usable patient area, SID and from experimental data, so that the power threshold may be indicative of the positive presence of the DR sensor within the usable patient area of a specific mobile unit 10. In this manner, if the average power calculated at step S202 is lower than the threshold power, a determination can be made as to whether the DR sensor is within the usable patient area or not. Accordingly, if the power average is below the power threshold (NO at S202) it can be assumed that the DR sensor in either not within the usable patient area or is being blocked by some obstacle. Thus, as step S204 the process returns to step S106 with a result indicating that the DR sensor should be moved and placed within the usable patient area. This process can be iteratively repeated until a signal received from the DR sensor 30 reaches an average ($P_{av}$) greater than the predetermined threshold.

On the other hand, when it is determined at step S204 that the average ($P_{av}$) of the power received at the antenna system 20 is greater than the threshold power (YES at S204), the flow process may directly proceed to step S208 and return to step S106 with a positive and certain determination that the DR sensor 30 is within the usable patient area. Optionally, however, the power levels received from each antenna 20a, 20b and 20c during the scanning process (step S102) may be used to calculate a specific position and/or distance of the DR sensor within the usable patient area. Specifically, an optional step S206 may be added to the process of FIG. 8, in which based on the power levels received from each antenna, it can be estimated in which of the radiation fields of antenna 20a, 20b or 20c the DR sensor may be located. The determination of the location of the DR sensor may, for example, be based on the power level of the signal received from the DR sensor, or it may be triangulated based on the different power levels received by each antenna. For example, when the DR sensor 30 is located within the region of radiation pattern 300c (FIGS. 4 and 5) and in direct line of sight with antenna 20c, it is likely that the power density levels received at antenna 20c may be higher than the power density levels received at antennas 20a or 20b (e.g., see test results in FIGS. 9A-9C). Thus, it may possible to reliably determine the location and/or distance of the DR sensor 30, when it is located within the usable patient area. In this manner, at step S208, the flow process of FIG. 8 can not only return a positive identification that the DR sensor is within the usable patient area AP, but it can also return the exact position of the DR sensor itself.

Returning now to FIG. 7, once the position of the DR sensor 30 has been calculated at step S106, the flow process proceeds to step S108. In the case that step S106 has returned a result indicative that the DR sensor is not within the usable patient area, the determination in step S108 is negative (NO in S108) and flow process advances to step S112. At step S112, a warning may be provided, for example, via the monitor 45 warning an operator that an imaging operation cannot be preformed because the DR sensor 30 is not within the usable patient area. In addition, at step S114 an instruction may be provided to the operator to relocate the DR sensor 30 to an area within the usable patient area, and the process returns to step S102. When at step S108, a positive assessment is made that the DR sensor is indeed within the usable patient area, the process advances to step S110. At step S110, either confirmation is given to the operator to proceed with an imaging operation, or the flow process automatically proceeds to perform an imaging operation. More specifically, once the presence of the DR sensor 30 within the usable patient area AP has been positively confirmed by analyzing the strength of the signal link received at the distributed antenna system 20, a transfer of image data from the DR sensor 30 to the console 11 of mobile unit 10 can be made substantially without errors even in environments where high levels of interference and noise exists.

FIGS. 9A to 9D are graphs in which the power density and amplitude of signals emitted by the distributed antenna 20 have been plotted for each antenna and compared to other sources of interference and noise. Power amplitude is indicated on the abscissa in −dBm levels. The channels being measured are shown on the ordinate in ascending order from left to right. The Density View maps and displays how often a frequency/amplitude point is being used. The less trafficked frequency ranges will appear more transparent. An important feature of the graphs of FIGS. 9A to 9D is that it shows device-specific signatures which enables analysis of what types of electronics are emitting RF energy in the usable patient area.

Figure 9A:
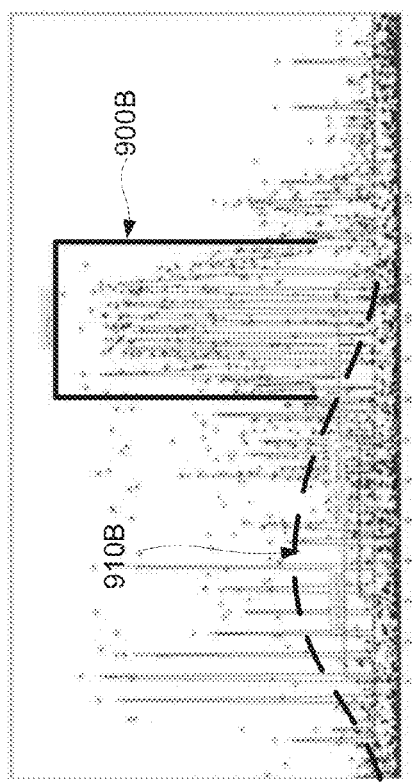
FIGS. 9A, 9B and 9C are power density graphs of antenna radiation levels measured at the front, left and right sides, respectively, of a radiographic imaging apparatus equipped with a distributed antenna system, in accordance with the first embodiment of the present invention.

FIG. 9A illustrates a power density view for the first antenna 20a (front internal antenna). For this test, a spectrum analyzer was positioned in front F of the mobile unit 10 at 72 inches from the X-Ray tube, and the measured amplitude level was shown to be −32 dbm peak. As illustrated in FIG. 9A, the strength of the power emitted by antenna 20a at its various channel is shown under the bracket 900A. The values of each channel are tabulated in Channel Table 1 below. The majority of the sources of interference, such as wireless routers, mobile computers (laptop) and the like are indicated as being located under curve 910A. All other sources of noise are shown as random dots, which permeate the entire spectrum of the illustrated results. From FIG. 9A and from the tabulated results in Cannel Table 1, however, it can be appreciated that the power level for antenna 20a are clearly higher and better defined than the surrounding noise and sources of interference.

| Channel Table 1 for front internal antenna | | | | | | | |
|---|---|---|---|---|---|---|---|
| Channel | Grade | Average | Access Points | Current | Duty Cycle | Max | Noise Floor |
| 1 | 99.4 | −74.5 | 0 | −101 | 0.3% | −50.0 | −102.5 |
| 2 | 99.3 | −73.5 | 0 | −101 | 0.3% | −48.5 | −102.5 |
| 3 | 99.1 | −71.5 | 1 | −101 | 0.4% | −47.0 | −102.5 |
| 4 | 98.8 | −71.5 | 0 | −100 | 0.5% | −47.0 | −102.0 |
| 13 | 98.8 | −73.5 | 0 | −94 | 0.6% | −49.5 | −102.5 |
| 5 | 98.2 | −71.0 | 1 | −87 | 0.8% | −47.0 | −102.0 |
| 6 | 97.9 | −71.0 | 1 | −87 | 0.9% | −47.0 | −102.0 |
| 12 | 97.3 | −70.0 | 0 | −94 | 1.3% | −46.5 | −102.0 |
| 7 | 97.2 | −71.0 | 0 | −87 | 1.3% | −47.5 | −102.0 |
| 8 | 96.0 | −69.5 | 0 | −76 | 1.9% | −46.5 | −102.0 |
| 11 | 95.9 | −68.0 | 0 | −76 | 1.9% | −45.0 | −102.0 |
| 9 | 95.5 | −68.0 | 1 | −76 | 2.1% | −45.0 | −102.0 |
| 10 | 95.2 | −68.0 | 1 | −76 | 2.2% | −44.5 | −102.0 |

The Channel Table 1 grades each Wi-Fi channel based on the RF activity within its given time span. This table is primarily used in pre-deployment of new wireless devices because it considers all RF noise occurring within Wi-Fi channels whether it is Wi-Fi or non-Wi-Fi. The Channel Grade is a weight for each freq/amp point based on how close it is to the center of the channel and its amplitude. The duty cycle is a relative score to help determine if a channel is usable or not. It measures how much RF activity is affecting the channel. It is weighted so that signals near the center of the channel have a greater effect on the duty cycle score. The average is a measurement of the average power within the channel frequency range. The max value is the highest amplitude point captured within the Wi-Fi channel frequency range.

Figure 9B:
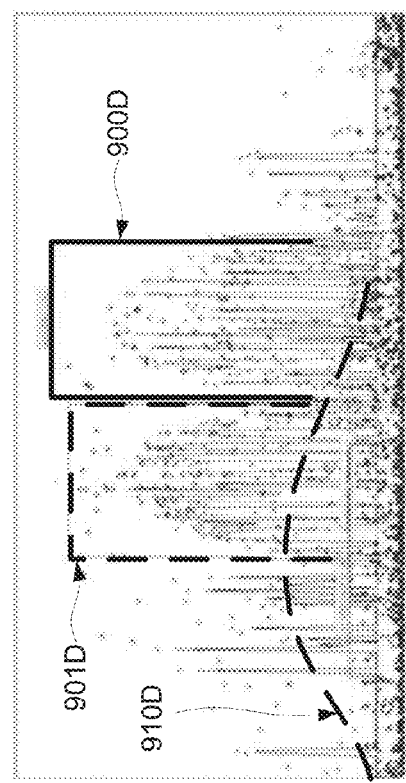

FIG. 9B illustrates a power density view for the second antenna 20b (left side L internal antenna). For this test, a spectrum analyzer was positioned at the left side L of the mobile unit 10 at 72 inches from the X-Ray tube, and the measured amplitude level was shown to be −32 dbm peak. As illustrated in FIG. 9B, the strength of the power emitted by antenna 20b at its various channels is shown under the bracket 900B. The values of each channel are tabulated in Channel Table 2 below. The majority of the sources of interference are indicated as being located under the curve 910B. All other sources of noise are shown as random dots, which permeate the entire spectrum (all channels) of the illustrated results. From FIG. 9C and from the tabulated results in Cannel Table 3 it can be shown that the power level for signals emitted from antenna 20c is clearly higher and better defined than the surrounding noise and sources of interference.

Channel Table 2 for left side internal antenna

| Channel | Grade | Average | Access Points | Current | Duty Cycle | Max | Noise Floor |
|---|---|---|---|---|---|---|---|
| 1 | 99.6 | −72.5 | 0 | −101 | 0.2% | −51.0 | −102.5 |
| 2 | 99.3 | −71.5 | 0 | −101 | 0.3% | −49.0 | −102.5 |
| 3 | 99.2 | −72.5 | 1 | −101 | 0.4% | −49.5 | −102.5 |
| 4 | 98.8 | −73.0 | 0 | −101 | 0.6% | −49.5 | −102.5 |
| 5 | 98.1 | −73.0 | 1 | −97 | 0.8% | −49.5 | −102.0 |
| 13 | 98.2 | −75.5 | 0 | −100 | 0.9% | −53.5 | −102.5 |
| 6 | 97.5 | −71.5 | 1 | −97 | 1.0% | −49.0 | −102.0 |
| 12 | 96.5 | −67.5 | 0 | −63 | 1.5% | −47.0 | −102.0 |
| 7 | 96.6 | −69.5 | 0 | −97 | 1.5% | −48.0 | −102.0 |
| 8 | 95.4 | −66.5 | 0 | −63 | 2.0% | −46.5 | −102.0 |
| 11 | 95.0 | −65.5 | 0 | −63 | 2.1% | −45.5 | −101.5 |
| 9 | 94.8 | −65.0 | 1 | −63 | 2.2% | −44.5 | −101.5 |
| 10 | 94.4 | −65.0 | 1 | −63 | 2.4% | −44.5 | −101.5 |

Figure 9C:
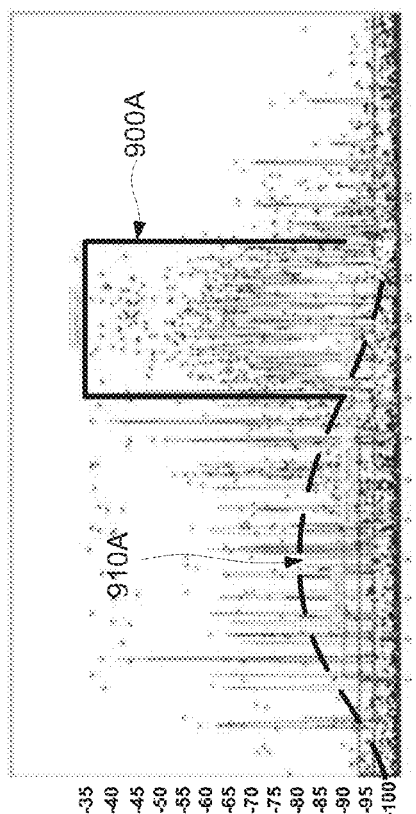

FIG. 9C illustrates a power density view for the third antenna 20c (right side internal antenna). For this test, a spectrum analyzer was positioned at the right sided R of the mobile unit 10 at 72 inches from the X-Ray tube, and the measured amplitude level was shown to be −32 dbm peak. As illustrated in FIG. 9C, the strength of the power emitted by antenna 20b at its various preferred channels is shown under the bracket 900C. The values of each channel are tabulated in Channel Table 3 below. The majority of the sources of interference are indicated as being located under curve 910C. All other sources of noise are shown as random dots, which permeate the entire spectrum (all channels) of the illustrated results. From FIG. 9C and from the tabulated results in Cannel Table 3 it can be appreciated that the power level for antenna 20c, similar to the power level of antennas 20a and 20b, is clearly higher and better defined than the surrounding levels of noise and interference.

Channel Table 3 for right side internal antenna

| Channel | Grade | Average | Access Points | Current | Duty Cycle | Max | Noise Floor |
|---|---|---|---|---|---|---|---|
| 1 | 99.4 | −72.5 | 0 | −101 | 0.3% | −47.5 | −102.5 |
| 2 | 99.3 | −71.5 | 0 | −101 | 0.3% | −46.0 | −102.5 |
| 3 | 99.2 | −72.0 | 1 | −101 | 0.4% | −45.5 | −102.5 |
| 4 | 98.8 | −72.5 | 0 | −101 | 0.6% | −45.5 | −102.5 |
| 13 | 98.2 | −75.5 | 0 | −99 | 0.9% | −48.0 | −102.5 |
| 5 | 98.2 | −73.0 | 1 | −101 | 0.8% | −45.0 | −102.0 |
| 6 | 97.6 | −72.5 | 1 | −101 | 1.0% | −44.5 | −102.0 |
| 12 | 96.5 | −67.0 | 0 | −99 | 1.6% | −44.0 | −102.0 |
| 7 | 96.7 | −71.0 | 0 | −102 | 1.4% | −44.0 | −102.0 |
| 8 | 95.5 | −67.5 | 0 | −61 | 2.0% | −43.0 | −102.0 |
| 11 | 95.0 | −65.5 | 0 | −61 | 2.2% | −42.5 | −101.5 |
| 9 | 94.8 | −65.5 | 1 | −61 | 2.2% | −41.5 | −101.5 |
| 10 | 94.5 | −65.0 | 1 | −61 | 2.4% | −41.5 | −101.5 |

Figure 9D:
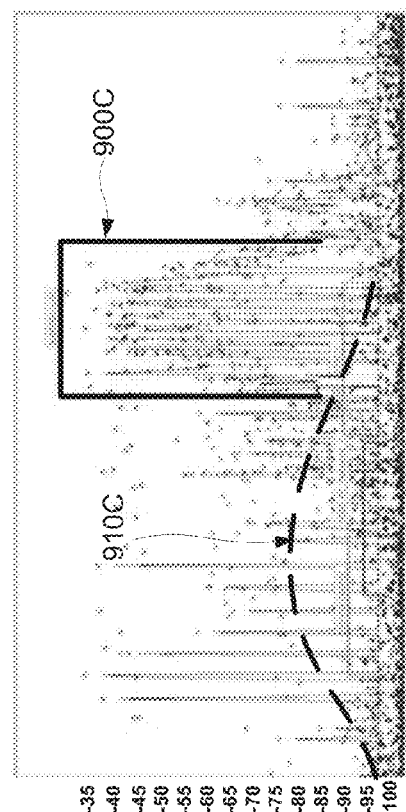
FIG. 9D is a power density graph of antenna radiation levels at a predetermined distance from a radiographic imaging apparatus equipped with a distributed antenna system in accordance with the first embodiment and compared to that of a second embodiment.

FIG. 9D Internal antenna compared to External antenna. The graph of FIG. 9B compares the Amplitude level of the two mobile units 10 equipped with the different antenna solutions. The signals within the dashed bracket 901D represents the mobile unit equipped with the external antenna solution (i.e., second embodiment illustrated in FIG. 5). The solid bracket 900A represents signal from the mobile unit 10 with the internal antenna solution (i.e., the first embodiment illustrated in FIGS. 1-4). In FIG. 9D, it can be observed that power levels for the antennas of both embodiments are substantially similar. Thus, it is considered that any of the disclosed embodiments represents a good solution to conventional problems discussed in the Background section of the invention.

While the present invention has been described with reference to exemplary embodiments, persons having ordinary skill in the art will appreciate that many variations are possible within the scope of the examples described herein. For example, although the distributed antenna system has been described as including three antennas, one of ordinary skill in the art will appreciate that a different number of antennas may be used. Thus, the distributed antenna system is not limited to a specific number of antennas. Similarly, although the placement of the antennas has been described as being inside the housing and located to face the usable patient area, other locations may also be used. For example, flexible antennas can be distributed on the outside of the housing 13 at the already described predetermined locations, and the housing itself may be used as an RF reflecting surface to direct the RF field towards the patient usable area, as described above. Moreover, although the distributed antenna system has been described as being applied to radiographic mobile unit, it can also be applied to a fixed radiographic apparatus, such as a ceiling mounted radiographic imaging apparatus. Thus, it should be understood that structural and functional modifications may be made without departing from the scope of the following claims to which it should be accorded the broadest reasonable interpretation.

What is claimed is:

1. A radiographic imaging apparatus, comprising:
   a mobile base station having a chassis, a housing, and control circuitry enclosed between the chassis and the housing; the mobile base station having a front side defining a patient area and a rear side defining an operator area;
   a plurality of antennas arranged on the chassis adjacent to the control circuitry and enclosed by the housing of the mobile base station and configured to perform wireless communication with an x-ray detector, and
   a control unit configured to transmit control signals from the mobile base station to the x-ray detector and receive image data from the x-ray detector via the plurality of antennas,
   wherein, before initiating an imaging operation with the x-ray detector, the control unit is configured to scan for a signal from the x-ray detector and to determine that the x-ray detector should be moved within the patient area in a case where a power level of the signal detected by the plurality of antennas is lower than a predetermined threshold.

2. The radiographic imaging apparatus according to claim 1, further comprising:
   an x-ray radiation source configured to irradiate a subject with x-ray radiation;
   wherein the control unit is configured to control the plurality of antennas to receive from the x-ray detector image data corresponding to the x-ray radiation that has passed through the subject.

3. The radiographic imaging apparatus according to claim 1, wherein the control unit is configured to combine radio frequency fields of each of the plurality of antennas to form a communication range within which the plurality of antennas establish the wireless communication with the x-ray detector from any point within the patient area, and
   wherein the communication range is an antenna sector substantially equal to 180 degrees centered around a barycentric position of the plurality of antennas.

4. The radiographic imaging apparatus according to claim 3, further comprising:
   a vertical column attached to the chassis of the mobile base station;

a movable arm attached to the vertical column; and
an x-ray radiation source attached to a distal end of the movable arm,
wherein the communication range is limited to a predetermined distance between the mobile base station and the x-ray detector, the predetermined distance being equal to a standard source to image detector distance plus the length of the movable arm.

5. The radiographic imaging apparatus according to claim 1, wherein the housing of the mobile base station is made of radio frequency (RF) transparent material.

6. The radiographic imaging apparatus according to claim 1, wherein the plurality of antennas enclosed within the housing of the mobile base station establish wireless communication with the x-ray detector along a direct or indirect communication path from any point within the patient area.

7. The radiographic imaging apparatus according to claim 1, wherein the control unit is further configured to determine whether the x-ray detector is located within the patient area prior to initiating the imaging operation.

8. The radiographic imaging apparatus according to claim 1, wherein the plurality of antennas includes 3 antennas which are enclosed within the housing of the mobile base station at a predetermined distance from each other so as to draw a triangular footprint.

9. The radiographic imaging apparatus according to claim 1, wherein, among the plurality of antennas, a first antenna is arranged inside the housing at a front most part of the chassis, a second antenna is arranged inside the housing at a left most part of the chassis, and a third antenna is arranged inside the housing at a right most part of the chassis of the mobile base station.

10. The radiographic imaging apparatus according to claim 1, wherein the control unit is configured to, before initiating the imaging operation with the x-ray detector, iteratively repeat the scan for a signal from the x-ray detector and to determine that the x-ray detector should be moved until the power level of the signal detected by the plurality of antennas is higher that the predetermined threshold.

11. The radiographic imaging apparatus according to claim 1, wherein the control unit is configured to combine radio frequency fields of each of the plurality of antennas and perform wireless communication with the x-ray detector by a multiple input multiple output (MIMO) scheme, and
wherein the control unit is configured to receive the image data from the x-ray detector via the plurality of antennas simultaneously using separate channels according to the MIMO scheme.

12. A method of wireless communication between a radiographic imaging apparatus and an x-ray detector, the imaging apparatus including a mobile base station having a chassis, a housing, and control circuitry enclosed between the chassis and the housing, the method comprising:
arranging a plurality of antennas on the chassis of the mobile base station adjacent to the control circuitry so that the housing of the mobile base station encloses the plurality of antennas and the control circuitry thereinside;
combining radio frequency fields of each of the plurality of antennas to form a communication range within which the plurality of antennas establish wireless communication with the x-ray detector from any point within the communication range;
transmitting control signals from the mobile base station to the x-ray detector and receiving image data from the x-ray detector via the plurality of antennas; and
before initiating an imaging operation with the x-ray detector, controlling the plurality of antennas with a control unit to scan for a signal from the x-ray detector and to determine that the x-ray detector should be moved within the patient area in a case where a power level of the signal detected by the plurality of antennas is lower than a predetermined threshold.

13. A radiation imaging system, comprising:
an x-ray detector;
a mobile base station having a chassis, a housing, control circuitry and a computer, the control circuitry and the computer being enclosed between the chassis and the housing, the mobile base station having a front side defining a patient area and a rear side defining an operator area;
an x-ray radiation source attached to a movable arm, the movable arm being attached orthogonally to a column disposed on the chassis adjacent to the housing; and
a plurality of antennas arranged on the chassis adjacent to the control circuitry so as to be enclosed by the housing of the mobile base station,
wherein the computer is configured to control the plurality of antennas to transmit control signals from the mobile base station to the x-ray detector and receive image data from the x-ray detector, and
wherein, before initiating an imaging operation with the x-ray detector, the computer is configured to scan for a signal from the x-ray detector and to determine whether the x-ray detector should be moved within the patient area in response to determining that a power level of the signal detected by the plurality of antennas is lower than a predetermined threshold.

14. The radiation imaging system according to claim 13, wherein each of the plurality of antennas forms a communication field directed towards the patient area.

15. The radiation imaging system according to claim 13, wherein the antennas are positioned inside the housing and near the column so as to face the patient area, the patient area being a 180 degree sector surrounding the console,
wherein the 180 degree sector has a radius equivalent to a maximum length of the movable arm plus a predetermined source to image detector distance.

16. The radiation imaging system according to claim 13, wherein, among the plurality of antennas, a first antenna is located at the front side, a second antenna is located at the left side, and a third antenna is located at the right side of the chassis of the mobile base station.

17. The radiation imaging system according to claim 16, wherein a barycentric position is determined as the center of gravity or average position of the first, second and third antennas,
wherein the computer is configured to determine whether the radiation detector is positioned within the patient area at a predetermined distance from the barycentric position, and
wherein, in a case where the computer determines the radiation detector is not positioned within the patient area, the computer is configured to issue a warning.

18. The radiation imaging system according to claim 17, wherein the predetermined distance is no greater than the maximum length of the movable arm plus a standard source to radiation detector distance.

* * * * *